US010398674B2

(12) United States Patent
Lowe et al.

(10) Patent No.: US 10,398,674 B2
(45) Date of Patent: Sep. 3, 2019

(54) THERAPEUTIC AGENTS CONTAINING CANNABIS FLAVONOID DERIVATIVES TARGETING KINASES, SIRTUINS AND ONCOGENIC AGENTS FOR THE TREATMENT OF CANCERS

(71) Applicant: Flavocure Biotech LLC, Columbia, MD (US)

(72) Inventors: Henry Lowe, West Indies (JM); Ngeh J. Toyang, Columbia, MD (US)

( * ) Notice: Subject to any disclaimer, the term of this patent is extended or adjusted under 35 U.S.C. 154(b) by 0 days.

(21) Appl. No.: 15/567,118

(22) PCT Filed: Nov. 24, 2015

(86) PCT No.: PCT/US2015/062331
§ 371 (c)(1),
(2) Date: Oct. 17, 2017

(87) PCT Pub. No.: WO2016/178713
PCT Pub. Date: Nov. 10, 2016

(65) Prior Publication Data
US 2018/0098961 A1    Apr. 12, 2018

Related U.S. Application Data

(63) Continuation of application No. 14/835,198, filed on Aug. 25, 2015, now Pat. No. 9,687,469.
(Continued)

(51) Int. Cl.
*A61K 31/353* (2006.01)
*C07D 311/32* (2006.01)
*C07D 311/60* (2006.01)

(52) U.S. Cl.
CPC .......... *A61K 31/353* (2013.01); *C07D 311/32* (2013.01); *C07D 311/60* (2013.01)

(58) Field of Classification Search
CPC ....................................................... A61K 31/353
(Continued)

(56) References Cited

U.S. PATENT DOCUMENTS

2004/0033280 A1    2/2004  Whittle et al.
2004/0259813 A1*  12/2004  Zi et al. ................. A61K 31/12
(Continued)

OTHER PUBLICATIONS

Daskiewicz et al, J. Med. Chem. 2005, vol. 48, pp. 2790-2804. (Year: 2005).*
(Continued)

*Primary Examiner* — Craig D Ricci
*Assistant Examiner* — Janet L. Coppins
(74) *Attorney, Agent, or Firm* — Royal W. Craig; Gordon Feinblatt LLC

(57) ABSTRACT

An embodiment of the invention provides a cannabis-based flavonoid pharmaceutical composition including any one or more selected, from among the group of Apigenin, Cannflavin. A. Cannflavin B, Cannflavin C, Chrysoeriol, Cosmosiin, Flavocannabiside, Kaempferol, Luteolin, Myricetin, Orientin, Isoorientin (Homoorientin), Quercetin (+)-Taxifolin, Vitexin, and Isovitexin, or their synthases, for the prevention and treatment of certain cancers that can be treated by therapeutically targeting oncogenic factors including kinases, sirtuins, bromodomains, matrix metalloproteinases and BCL-2. Some of the cancers that can be treated by use of cannabis flavonoids based on the inhibition of these therapeutic targets include brain, breast, colon, renal, liver, lung, pancreatic, prostate, leukemia, melanoma as well as any other cancers that overexpress the oncogenic factors inhibited by the cannabis flavonoids identified herein.

2 Claims, 6 Drawing Sheets

Related U.S. Application Data

(60) Provisional application No. 62/156,228, filed on May 2, 2015.

(58) Field of Classification Search
USPC .......................................................... 514/456
See application file for complete search history.

(56) References Cited

U.S. PATENT DOCUMENTS

| | | |
|---|---|---|
| 2006/0084135 A1 | 4/2006 | Howitz et al. |
| 2010/0222437 A1 | 9/2010 | Munoz Blanco et al. |
| 2011/0117649 A1 | 5/2011 | Scheidt et al. |
| 2013/0303544 A1* | 11/2013 | Ding .................... C07D 311/30 |
| | | 514/254.11 |

OTHER PUBLICATIONS

Dong et al, Eur. J. Med. Chem. (2011). vol. 46, pp. 5949-5958. (Year: 2011).*
Wang et al, J. Nat. Prod. (2004), vol. 67, pp. 757-761. (Year: 2004).*
Yang et al, Filoterapia (2015), vol. 103, pp. 187-191. Available online Apr. 8, 2015. (Year: 2015).*
Manthey and Guthrie, J. Agric Food Chem (2002), vol. 50, pp. 5837-5843. (Year: 2002).*
Androutsopoulos et al—Comparative CYP1A1 and CYP1B1 substrate and inhibitor profile of dietary flavanoids; Bioorganic and Medicinal Chemistry, 19 (2011)—2842-2849.

* cited by examiner

THERAPEUTIC AGENTS CONTAINING CANNABIS FLAVONOID DERIVATIVES TARGETING KINASES, SIRTUINS AND ONCOGENIC AGENTS FOR THE TREATMENT OF CANCERS

CROSS-REFERENCE TO RELATED APPLICATIONS

The present application derives priority from U.S. Provisional Patent Application 62/156,228 filed 2 May 2015, and is a continuation-in-part of U.S. patent application Ser. No. 14/835,198 filed 25 Aug. 2015.

BACKGROUND OF THE INVENTION

1. Field of the Invention

The present invention relates to flavonoid derivatives and, more particularly, to cannabis flavonoid derivatives or the pharmaceutically acceptable salt thereof that may be used in a pharmaceutical composition for preventing and treating cancer.

2. Description of the Background

Flavonoids are common constituents of plants and cover a wide range of functions including acting as yellow pigments in petals and leaves to attract pollinating insects. They might also appear as bluish pigments (anthocyanins) to receive certain wavelengths of light, which permits the plant to be aware of the photoperiod. Many of these flavonoids also protect the plants by being involved in the filtering of harmful ultraviolet light. Some flavonoids play crucial roles in establishing symbiotic fungi, while at the same time they fight infections caused by pathogenic fungi.

Flavonoids have relevant pharmacological activities such as: antioxidant, antidiabetic, anti-inflammatory, antiallergic, antibiotic, antidiarrheal, CNS and against cancer.

Cannabis is credited to have several beneficial pharmacological properties. Unfortunately much attention on Cannabis is focused on its recreational use as a psychoactive drug. Studies have identified over twenty flavonoids in the Cannabis plant, such as: cannflavin A, cannflavin B, cannflavin C, chrysoeril, cosmosiin, flavocannabiside, vitexin, isovitexin, apigenin, kaempferol, myricetin, quercetin, luteolin, homoorientin and orientin. Turner, C. E., Elsohly, M. A., & Boeren, E. G., "Constituents of Cannabis Sativa L. XVII., A review of the natural constituents", *Journal of Natural Products*, 43(2), 169-234 (1980). The distribution of these flavonoids in the plant varies depending on the type of flavonoid. The total content of flavonoids in the Cannabis' leaves and flowers can reach 1-2.5% of its dry weight depending on environment factors and the variety of the plant. It is noteworthy to mention that even though cannflavin A has been isolated from other plant sources, it is only cannabis that has been shown to harbor all three natural cannflavins.

Cannabis flavonoids have been shown to have several pharmacological properties especially the most common flavonoids such as quercetin, apigenin, luteolin and kaempferol. ElSohly, M. A., Slade, D., "*Life Sciences*", 78(5), 539-548 (2005). Chemical constituents of marijuana: the complex mixture of natural cannabinoids). These more common flavonoids can be found in many other plants and as such are not unique to cannabis. Apart from the specific pharmacologic properties identified, cannabis flavonoids are thought to play synergistic roles with other metabolites in the plant. For example, some flavonoids are volatile, lipophilic, permeate membranes, and seem to retain pharmacological properties in cannabis smoke. Sauer, M. A., Rifka, S. M., Hawks, R. L., Cutler, G. B., & Loriaux, D. L., "*Journal of Pharmacology and Experimental Therapeutics*", 224(2), 404-407 (1983). Marijuana: interaction with the estrogen receptor. Flavonoids may modulate the pharmacokinetics of THC, via a mechanism shared by CBD, the inhibition of P450 3A11 and P450 3A4 enzymes. These two related enzymes metabolize environmental toxins from procarcinogens to their activated forms. P450-suppressing compounds as such serve as chemoprotective agents, shielding healthy cells from the activation of benzo[α]pyrene and aflatoxin B1. Offord, E. A., Macé, K., Avanti, O., & Pfeifer, A. M., "Mechanisms Involved In The Chemoprotective Effects Of Rosemary Extract Studied In Human Liver And Bronchial Cells". *Cancer Letters*, 114(1), 275-281, (1997). Benzo[α]pyrene and aflatoxin B1 are two procarcinogenic agents found in cannabis smoke. McPartland, J. M., & Pruitt, P. L., "*Alternative Therapies In Health And Medicine*", 5(4), 57 (1999). Side effects of pharmaceuticals not elicited by comparable herbal medicines: the case of tetrahydrocannabinol and marijuana. Cannabis flavonoids thus may be modulating the therapeutic effects of THC and CBDs by either synergistically enhancing desired pharmacologic effects or reducing detrimental effects. McPartland, J. M., Russo. E. B., "Cannabis *And Cannabis Extracts: Greater Than The Sum Of Their Parts?*", Journal of Cannabis Therapeutics, 1(3-4), 103-132 (2001).

There is a small amount of literature on the bioactivity of cannflavins and other closely related flavonoids isolated either from cannabis or from other plants. Barrett et al (1985) reported the inhibition properties of cannflavins on prostaglandins with implication on inflammation. Barrett, M. L., Gordon, D., Evans, F. J., "*Isolation From Cannabis Sativa L. Of Cannflavin—A Novel Inhibitor Of Prostaglandin Production*", Biochemical Pharmacology, 34(11), 2019-2024 (1985).

Blanco et al. (2008) reported on cannabidiol and denbinobin and their use for the prevention and treatment of gastrointestinal inflammatory diseases and for the prevention and treatment of gastrointestinal cancers. U.S. patent application Ser. No. 12/681,453 published 2 Sep. 2010. Radwan et al. (2008) reported antileishmanial activity for cannflavin A and cannflavin B. Radwan, M. M., ElSohly, M. A., Slade, D., Ahmed, S. A., Wilson, L, El-Alfy, A. T., Ross, S. A., "*Non-Cannabinoid Constituents From A High Potency Cannabis Sativa Variety*", Phytochemistry 69(14), 2627-2633 (2008). Brunelli, et al. (2009) reported that isocannflavin B induced autophagy in hormone sensitive breast cancer cells. Brunelli, E., Pinton, G., Bellini, P., Minassi, A., Appendino, G., & Moro, L., "*Flavonoid-Induced Autophagy In Hormone Sensitive Breast Cancer Cells*", Fitoterapia 80(6), 327-332 (2009). Li and Meng (2012) reported the use of the flavonoid Icaritin to treat estrogen receptor related disease. U.S. Pat. No. 8,252,835 issued 28 Aug. 2012. Meng et al. (2014) also reported the use of Icaritin to treat cancers. U.S. patent application Ser. No. 14/291,639 published 24 Dec. 2014. Apart from the autophagy activity on breast cancer reported by Brunelli and colleagues no other report was seen relating to anticancer activity of cannflavins. Cytotoxicity studies carried out by the US National Cancer Institute (NCI) using its 60 cancer cell line panel showed that cannflavin B was not cytotoxic against cancer cells (NSC:719330).

Despite the foregoing, there has been no prior effort to detail the targeting of kinases, sirtuins, matrix metalloproteinase, bromodomains and BCL-2 by the cannflavins or their analogs in the treatment of cancer. An oncogene is a gene that has the potential to cause cancer. In tumor cells, oncogenes are often mutated or expressed at high levels. Certain cancers overexpress certain oncogenic factors, and these oncogenic factors may be useful therapeutic targets. However, different cancer lines respond differently to various oncogenic agents and that the response of an outgrowth line to a combination of several such agents is unpredicatble. The absence of knowledge regarding the use of cannflavins against these important therapeutic targets prompted the present inventors to evaluate the effect of cannflavins against several kinases, sirtuins, matrix metalloproteinases, bromodomains and BCL-2, with excellent results.

SUMMARY OF THE INVENTION

It is another object to provide a method for the prevention and treatment of cancer using specific cannabis-based flavonoid pharmaceutical compositions.

It is another object to provide a method for isolating specific cannabis-based flavonoid pharmaceutical compositions from raw plant material that are biologically active in the prevention and treatment of cancer.

It is still another object to provide a method for synthesizing said specific cannabis-based flavonoid pharmaceutical compositions and a synthase.

In according with the foregoing objects, the inventors have successfully synthesized cannflavins including cannflavin A, cannflavin B and cannflavin C and their derivatives and have demonstrated their anti-cancer efficacy in various assays including with specific focus on identifying their therapeutic targets. The present invention relates to the use of the newly synthesized flavonoids alone or in combination with other bioactive compounds to treat or prevent cancers.

In accordance with the foregoing objects, the present invention provides a flavonoid-based pharmaceutical composition for the prevention and treatment of cancer having the structure of the general formula shown below (see also FIG. 1) or a pharmaceutically acceptable salt thereof.

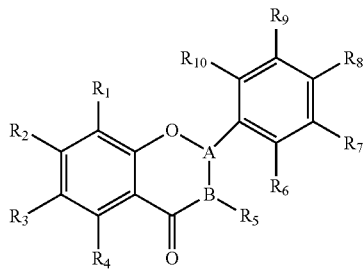

wherein,

R1-R10 may be any one or more substituents selected from the group consisting of a hydrogen molecule (H), a hydroxide molecule (OH), a methyl group comprising one carbon atom bonded to three hydrogen atoms (CH3), an alkoxy group (—OCH3), a carboxyl group (COOH), chlorine (Cl), Bromine (Br), Fluorine (F), Glutamic acid (Glu), geranyl chain, prenyl chain and any salts or derivatives of the foregoing. A and B may each be either a single or double bond.

A method for the prevention and treatment of cancer using the specific cannabis-based flavonoid pharmaceutical compositions is also disclosed, as well as a method for isolating the specific flavonoid-based pharmaceutical compositions from raw plant material, and a method for synthesizing said flavonoid-based pharmaceutical compositions.

The present invention is described in greater detail in the detailed description of the invention, and the appended drawings. Additional features and advantages of the invention will be set forth in the description that follows, will be apparent from the description, or may be learned by practicing the invention.

BRIEF DESCRIPTION OF THE DRAWINGS

Other objects, features, and advantages of the present invention will become more apparent from the following detailed description of the preferred embodiments and certain modifications thereof when taken together with the accompanying drawings in which.

DETAILED DESCRIPTION OF THE PREFERRED EMBODIMENTS

Figure 1:
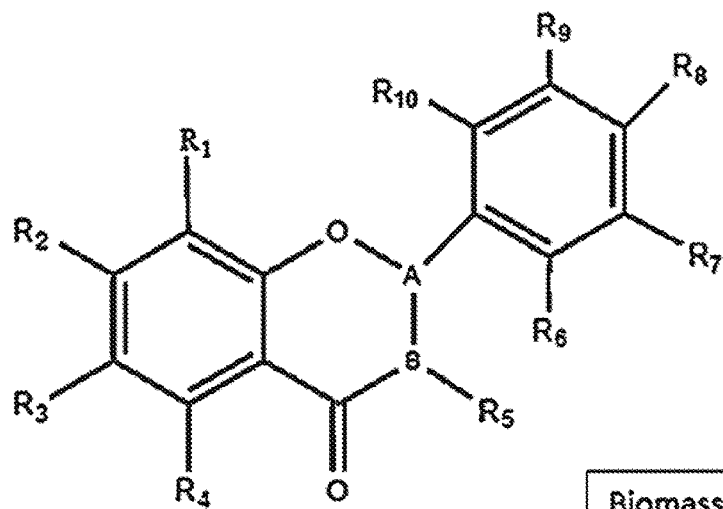
FIG. 1 is an illustration of the general cannabis-based flavonoid pharmaceutical compositions according to the present invention.

Reference will now be made in detail to preferred embodiments of the present invention, examples of which are illustrated in the accompanying drawings. Wherever possible, the same reference numbers will be used throughout the drawings to refer to the same or like parts.

An oncogene is herein defined as a gene that has the potential to cause cancer. In tumor cells, oncogenes are often mutated or expressed at high levels. Certain cancers overexpress certain oncogenic factors including kinases, sirtuins, bromodomains, matrix metalloproteinases and BCL-2. Thus, these particular oncogenic factors are identified as useful therapeutic targets for purposes of the present invention.

Given the foregoing targets, some of the cancers that can be treated by use of cannabis flavonoids based on the inhibition of these therapeutic targets include brain, breast, colon, renal, liver, lung, pancreatic, prostate, leukemia, melanoma as well as any other cancers that overexpress the oncogenic factors inhibited The present invention is a group of cannabis-based flavonoid pharmaceutical compositions selected from among the group of Apigenin, Cannflavin A, Cannflavin B, Cannflavin C, Chrysoeriol, Cosmosiin, Flavocannabiside, Kaempferol, Luteolin, Myricetin, Orientin, Isoorientin (Homoorientin), Quercetin, (+)-Taxifolin, Vitexin, and Isovitexin, useful for the prevention and treatment of certain cancers especially those that can be treated by targeting kinases, sirtuins, bromodomains, matrix metalloproteinases and BCL-2 which have been identified to be useful therapeutic targets for some cancers. Some of the cancers that can be treated by use of cannabis flavonoids based on the inhibition of these therapeutic targets include brain, breast, colon, renal, liver, lung, pancreatic, prostate, leukemia, melanoma as well as any other cancers that overexpress the oncogenic factors inhibited by the cannabis flavonoids identified under this invention.

The cannabis-based flavonoid pharmaceutical composition for the prevention and treatment of cancers has the structure of the general formula shown below (see also FIG. 1), or a pharmaceutically acceptable salt thereof.

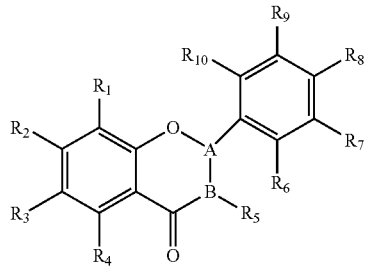

wherein,

R1-R10 may be any one or more substituents selected from the group consisting of a hydrogen molecule (H), a hydroxide molecule (OH), a methyl group comprising one carbon atom bonded to three hydrogen atoms (CH3), an all oxy group (—OCH3), a carboxyl group (COOH), chlorine (Cl), Bromine (Br), Fluorine (F), Glutamic acid (Gln), and any salts or derivatives of the foregoing. A and B may each be either a single or double bond.

In an embodiment, a method for the prevention and treatment of cancer using the specific cannabis-based flavonoid pharmaceutical compositions above is also disclosed. Administration may be by various routes including oral, rectal or intravenous, epidural muscle, subcutaneous, intrauterine, or blood vessels in the brain (intracerebroventricular) injections. The flavonoid derivatives of the general formula (FIG. 1) according to the present invention and a pharmaceutically acceptable salt thereof may be administered in an effective dose, depending on the patient's condition and body weight, extent of disease, drug form, route of administration, and duration, within a range of from 0.1 to 500 mg between 1-6 times a day. Of course, most dosages will be by a carrier. The specific dose level and carrier for patients can be changed according to the patient's weight, age, gender, health status, diet, time of administration, method of administration, rate of excretion, and the severity of disease.

The composition may be formulated for external topical application, oral dosage such as powders, granules, tablets, capsules, suspensions, emulsions, syrups, aerosols, suppositories, or in the form of a sterile injectable solution. Acceptable carriers and excipients may comprise lactose, dextrose, sucrose, sorbitol, mannitol, xylitol, erythritol, maltitol, starches, gum acacia, alginate, gelatin, calcium phosphate, calcium silicate, cellulose, methyl cellulose, microcrystalline cellulose, polyvinylpyrrolidone, water, methyl benzoate, propyl benzoate, talc, magnesium stearate, and mineral oil.

Bioactivity

Bioactivity of the above-described compounds were verified and is presented in Tables 1, 2, and 3 below:

TABLE 1

| | Kinase | | | | |
|---|---|---|---|---|---|
| | FBL-03A | FBL-03B | FBL-03C | FBL-03D | FBL-03G |
| | | | $IC_{50}$ (nM) | | |
| Aurora A | 730 | 12 | 21 | >30000 | 1090 |
| BIKE | >20000 | >20000 | 21 | >30000 | >20000 |
| CK2a | 740 | 768 | 58 | >30000 | 38 |
| CK2a2 | 350 | 477 | 19 | >30000 | 9.7 |
| c-Kit(Y823D) | >20000 | 244 | >20000 | >30000 | 84 |
| c-Kit(D820Y) | >20000 | 1280 | >20000 | >30000 | 113 |
| DRAK2 | >20000 | <1000 | 980 | >30000 | >10000 |
| DYRK1/DYRK1A | >20000 | <1000 | 620 | >30000 | 36 |
| DYRK1B | >20000 | 1670 | 6400 | >30000 | 22.8 |
| EFGR(L858R, T7790M) | >20000 | >1000 | 680 | >30000 | >1000 |
| EPHB6 | >20000 | >1000 | 270 | >30000 | >1000 |
| FGR | >20000 | 224 | >20000 | >30000 | 880 |
| FLT3 | >20000 | 41.9 | >20000 | >30000 | 44 |
| FLT3(D835Y) | >20000 | 12.7 | >20000 | >30000 | 45 |
| FLT3(D835V) | 220 | <1000 | 190 | >30000 | <1000 |
| FLT3(ITD) | >20000 | 57 | >20000 | >30000 | <1000 |
| FLT4 (VEGFR3) | 330 | 9.3 | >20000 | >30000 | 4220 |
| FMS/CSF1R | 1500 | 199 | 1200 | >30000 | 4 |
| JAK3 | >20000 | >1000 | 780 | >30000 | >20000 |
| KIT | 350 | <1000 | >1000 | >30000 | <1000 |
| KIT(L576P) | 180 | <1000 | >1000 | >30000 | <1000 |
| KIT(V559D) | 200 | <1000 | >1000 | >30000 | <1000 |
| MELK | >20000 | 232 | >1000 | >30000 | 105 |
| MEK5 | 140 | >1000 | 84 | >30000 | >1000 |
| PASK | >20000 | 2060 | >20000 | >30000 | 116 |
| PDGFRa | — | 982 | — | >30000 | 5920 |
| PDGFRa (T674I) | — | 0.92 | >1000 | >30000 | 2360 |
| PDGFRB | 330 | 1160 | >1000 | >30000 | 3310 |
| PIK3CA (1800L) | >20000 | | 780 | >30000 | >20000 |
| PIK4CB | 670 | | >1000 | >30000 | >20000 |
| PIM-1 | >20000 | | >1000 | >30000 | 78 |
| PIM-3 | >20000 | 173 | >1000 | >30000 | 35 |
| PIP5K1A | >20000 | >10000 | 360 | >30000 | >20000 |
| RIOK1 | >20000 | >10000 | 340 | >30000 | >20000 |
| RIOK3 | >20000 | >10000 | 280 | >30000 | >20000 |
| SIK2 | >20000 | >10000 | >1000 | >30000 | 63 |
| SRPK1 | >20000 | >10000 | 300 | >30000 | >10000 |
| TNIK | >20000 | 152 | >1000 | >30000 | 115 |

TABLE 2

| Activity | FBL-03A | FBL-03B | FBL-03C | FBL-03D | FBL-03G |
|---|---|---|---|---|---|
| | | | $IC_{50}$ (μM) | | |
| SIRT | | | | | |
| SIRT-1 | 19.00 | 27.40 | 39.50 | — | — |
| SIRT-2 | 2.57 | 10.80 | 14.00 | 2.38 | 24.10 |
| SIRT-3 | 94.90 | 77.00 | 65.40 | — | 66.40 |
| SIRT-5 | 123.00 | 104.00 | 132.00 | — | 974.00 |
| Bromodomain | | | | | |
| BRD2 | NT | 9.52 | NT | NT | 12.00 |
| BRD3 | NT | 7.05 | NT | NT | 8.69 |
| BRD4 | NT | 10.40 | NT | NT | 6.14 |
| Matrix metalloproteinase | | | | | |

TABLE 2-continued

| Activity | FBL-03A | FBL-03B | FBL-03C | FBL-03D | FBL-03G |
|---|---|---|---|---|---|
| | | | $IC_{50}$ (μM) | | |
| MMP-2 | NT | 115.00 | NT | NT | 6.64 |
| MMP-3 | NT | — | NT | NT | 66.30 |
| MMP-7 | NT | 17.52 | NT | NT | 3.35 |
| MMP-9 | NT | — | NT | NT | 85.40 |
| BCL-2 | NT | — | NT | NT | 2.49 |
| BCL-XL | NT | — | NT | NT | — |

TABLE 3

| Cell Line | FBL-03A | FBL-03B | FBL-03C | FBL-03D | FBL-03G |
|---|---|---|---|---|---|
| | | | $IC_{50}$ (μM) | | |
| A498 (Kidney) | 17 | NT | 14 | NT | NT |
| A549 (Lung) | 17 | NT | 9.4 | NT | NT |
| CFPAC-1 (Pancreatic) | 12 | 17 | 12 | NT | 14.32 |
| CMK (leukemia) | NT | 11.60 | NT | NT | 1.78 |
| COLO-205 (Colon) | 27 | NT | 17 | NT | NT |
| DLD-1 (Colon) | 15 | NT | 13 | NT | NT |
| HC-1 (Leukemia) | NT | 29.70 | NT | NT | 5.00 |
| HeLa (cervical) | NT | 10.40 | NT | NT | 2.53 |
| IGROV-1 (Ovarian) | 29 | | 15 | NT | NT |
| KMS-11 (Multiple myeloma) | NT | NT | NT | NT | NT |
| MCF-7 (Breast) | 17 | NT | 12 | NT | NT |
| MiaPaca-2 (Pancreatic) | 16 | NT | 9.5 | NT | NT |
| MOLT-4 (Leukemia) | NT | 13.20 | NT | NT | 20.00 |
| MV4-11 (Leukemia) | NT | 1.43 | NT | NT | 3.1 |
| NCI-H69 (Small lung) | 16 | 11 | 18 | NT | 9.5 |
| PC-3 (Prostate) | 26 | NT | 20 | NT | NT |
| RL (Lymphoma) | 5.9 | NT | 12 | NT | NT |
| SNU-16 (Stomach) | NT | 15.00 | NT | NT | 4.09 |
| U2-OS (Bone) | NT | 19.40 | NT | NT | 8.70 |
| UACC-62 (Melanoma) | 27 | NT | 14 | NT | NT |
| U87 (Glioma) | 34.00 | 6.20 | 12.50 | NT | 5.46 |

Isolation and Synthesis

A method for isolating the specific cannabis-based flavonoid pharmaceutical compositions from raw plant material is also disclosed. The isolation was realized according to the scheme shown in FIG. 2.

At step 10 an appropriate amount of plant biomass is collected. For present purposes, Cannabis sativa plants were collected by hand. See, Radwan, M. M., ElSohly, M. A., Slade, D., Ahmed, S. A., Wilson, L., El-Alfy, A. T., Khan, I. A., Ross, S. A., "*Non-Cannabinoid Constituents From A High Potency Cannabis Sativa Variety*", Phytochemistry 69, 2627-2633 (2008) and Radwan, M. M., Ross, S. A., Slade, D., Ahmed, S. A., Zulfiqar, F., ElSohly, M. A., "*Isolation And Characterization Of New Cannabis Constituents From A High Potency Variety*", Planta Med. 74, 267-272 (2008). The collected plant material was air dried under shade and pulverized into powder.

At step 20 the powder is subjected to supercritical fluid extraction (SFE) by which carbon dioxide ($CO^2$) is used for separating one component (the extractant) from another (the matrix). The extract is evaporated to dryness resulting in a green residue.

At step 30, for experimental purposes, a bioassay-guided fractionation was employed, using a standard protocol to isolate a pure chemical agent from its natural origin. This entailed a step-by-step separation of extracted components based on differences in their physicochemical properties, and assessing all their biological activity. The extracted components may, for example, be fractionated by dry column flash chromatography on Si gel using hexane/$CH_2Cl$/ethyl acetate and mixtures of increasing polarity to yield different fractions. The sample is then degassed by ultra-sonication to yield an insoluble solid, which solid is then filtered. The sample may then be subjected to high performance liquid chromatography (HPLC) using a column Phenomenex Luna™ C18, 5 μm, 2×50 mm; eluent, acetonitrile with 0.05% MeOH to confirm the presence of the various fractions.

At step 40, bioactivity of the extracts were verified by an anticancer cell proliferation assay as described above. This identified the bioactive flavonoids from all the supercritical fluid extracts (SFE). As reported previously, the identified cannabis-based flavonoid extracts showed activity against several cancer cell lines including brain, breast, Kaposi sarcoma, leukemia, lung, melanoma, ovarian, pancreatic, colon and prostate cancer.

At step 50 Nuclear Magnetic Resonance Spectroscopy and mass spectrometry (NMR/MS) was performed and the interpreted spectra were consistent with cannabis-based flavonoid compositions as identified above, as illustrated in step 60.

Figure 2:
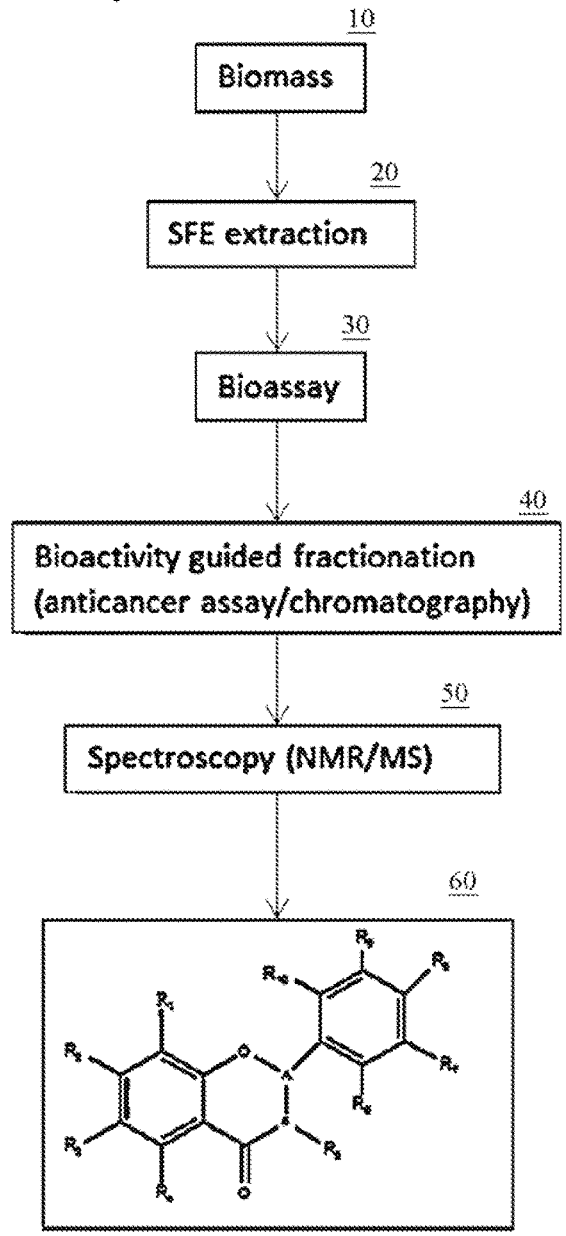
FIG. 2 is a flow diagram illustrating a suitable method for isolating the specific cannabis-based flavonoid pharmaceutical compositions from raw plant material.

Synthesis Given the known structure of the general formula of FIG. 1 and the isolate of FIG. 2, a method for synthesizing the same becomes possible. The bioactive cannabis-based flavonoid pharmaceutical composition may be synthesized by the phenylpropanoid metabolic pathway in which the amino acid phenylalanine is used to produce 4-coumaroyl-CoA.

Figure 3:
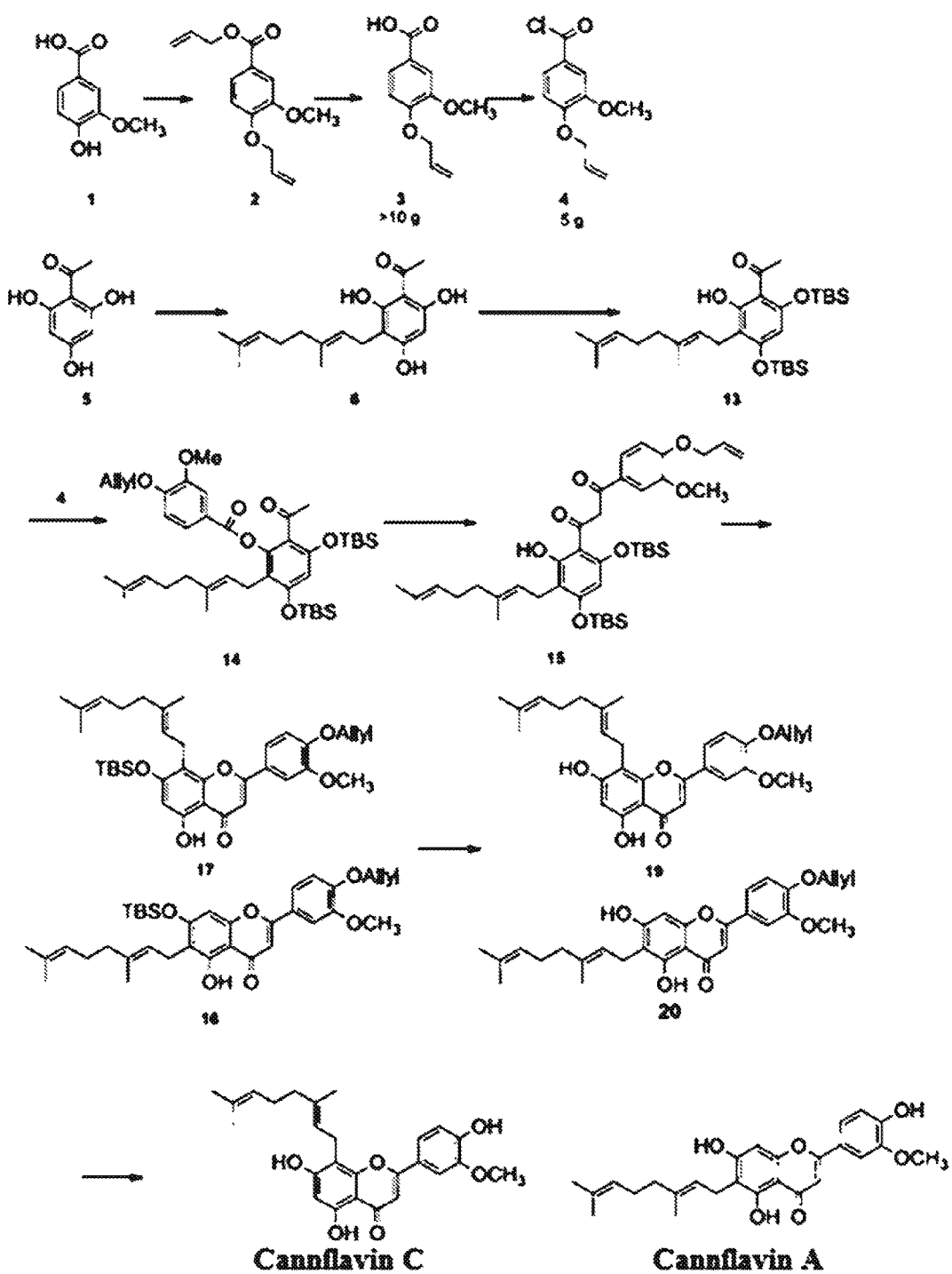
FIG. 3 is a process diagram illustrating a suitable synthesis approach.
Figure 3:
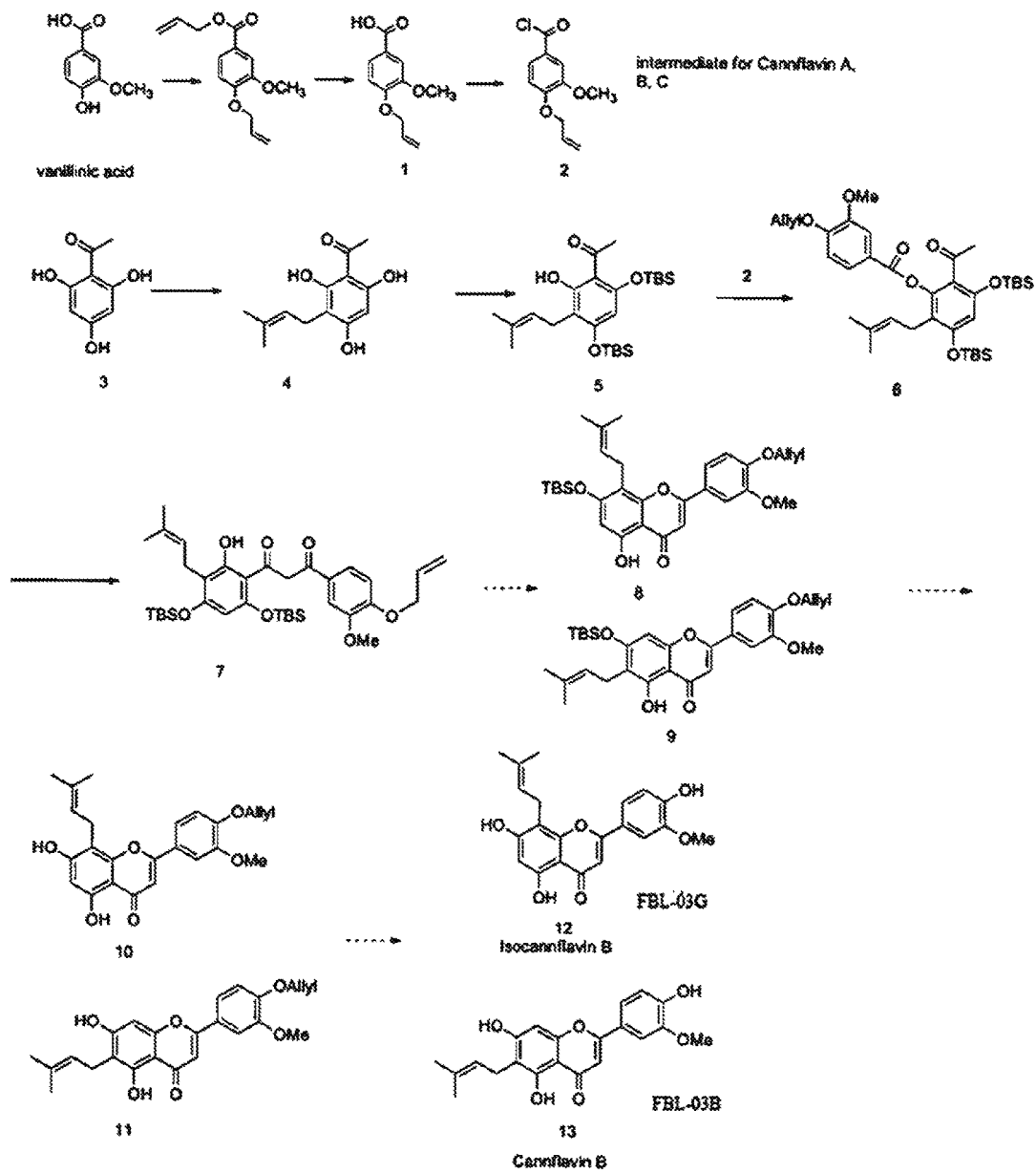
Figure 4:
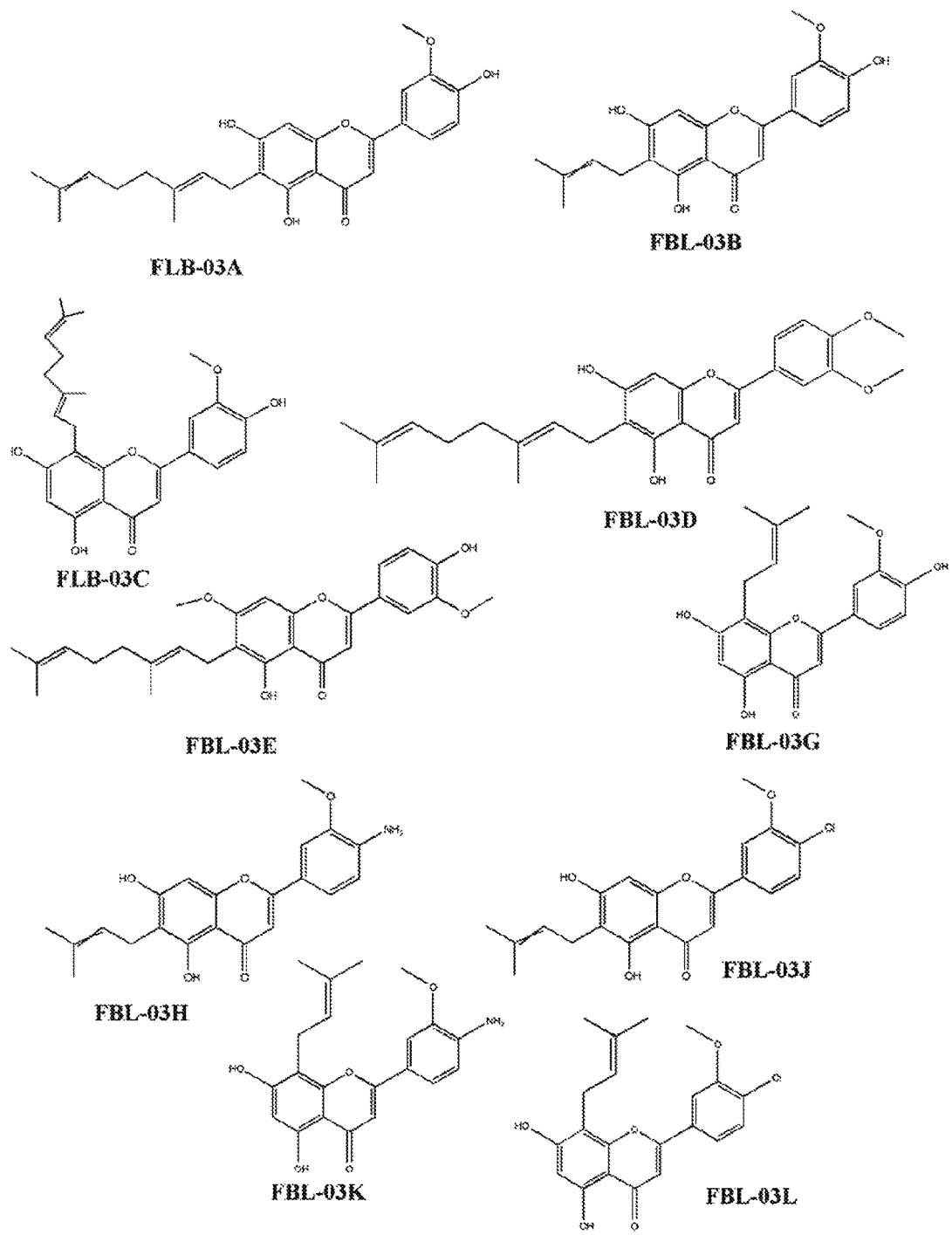
FIG. 4 is an illustration of the specific isolated cannabis-based flavonoid pharmaceutical compositions including Flavone, Flavanone and Flavanol isolates, according to the present invention.

FIG. 3 is a process diagram illustrating a suitable synthesis approach for the cannflavins. The 2',4',6'-Trihydroxyacetophenone was the major starting material and the synthesis was carried out using art known to the industry with modifications yielded the flavonoid backbone which contains two phenyl rings. Conjugate ring-closure of chalcones results in the familiar form of flavonoids, the three-ringed structure of a flavone. The metabolic pathway continues through a series of enzymatic modifications to yield the desired Flavone, Flavanone and Flavanol as identified above and as shown in step 60 (FIG. 3). The specific Flavone, Flavanone and Flavanol isolates are shown in step FIG. 5.

For background see Minassi, A., Giana, A., Ech-Chahad, A., & Appendino, G. "*A regiodivergent synthesis of ring A C-prenylflavones*", Organic Letters 10(11), 2267-2270 (2008). Of course, one skilled in the art will readily understand that other methods for synthesis are possible, such as the asymmetric methods set forth in Nibbs, A E; Scheidt, K A, "*Asymmetric Methods for the Synthesis of Flavanones, Chromanones, and Azaflavnones*", European Journal Of Organic Chemistry, 449-462. doi:10.1002/ejoc.201101228. PMC 3412359. PMID 22876166 (2012).

Bioactivity Assays

Cannabis flavonoids and their analogs were subjected to kinase inhibition assay. The compounds were first screened at a single concentration of 10 μM in the primary assay. Compounds inhibiting at least 70% of specific kinases were subjected to further screening to determine kd/$IC_{50}$ values. To determine the kd or $IC_{50}$ values, competition binding assays were established, authenticated and executed as described previously. Fabian et al., "A Small Molecule-Kinase Interaction Map For Clinical Kinase Inhibitors.", Nat Biotechnol, 23(3):329-36, Epub (2005). See also, Karaman et al., "A Quantitative Analysis Of Kinase Inhibitor Selectivity", Nat. Biotechnol. January, 26(1):127-32. doi: 10.1038/nbt1358 (2008). For most assays, kinases were fused to T7 phage strains (Fabian, supra) and for the other assays, kinases were produced in HEK-293 cells after which they were tagged with DNA for quantitative PCR detection. In general, full-length constructs were used for small, single domain kinases, and catalytic domain constructs for large multi-domain kinases. The binding assays utilized streptavidin-coated magnetic beads treated with biotinylated small molecule ligands for 30 minutes at room temperature which generated affinity resins for the kinase assays. The liganded beads were blocked with excess biotin and washed with blocking buffer (SeaBlock (Pierce), 1% BSA, 0.05% Tween 20, 1 mM DTT) to remove unbound ligand and to reduce non-specific phage binding. Binding reactions were assembled by combining kinases, liganded affinity beads, and test compounds in 1× binding buffer (20% SeaBlock, 0.17×PBS, 0.05% Tween 20, 6 mM DTT). Test compounds were prepared as 40× stocks in 100% DMSO and diluted directly into the assay (Final DMSO concentration=2.5%). All reactions were performed in polypropylene 384-well plates in a final volume of 0.04 ml. The assay plates were incubated at room temperature with shaking for 1 hour and the affinity beads were washed with wash buffer (1×PBS, 0.05% Tween 20). The beads were then re-suspended in elution buffer (1×PBS, 0.05% Tween 20, 0.5 µM non-biotinylated affinity ligand) and incubated at room temperature with shaking for 30 minutes. The kinase concentration in the eluates was measured by quantitative PCR. An illustration of the kinase interaction process is presented below. $Kd/IC_{50}$ values were determined using a standard dose response curve using the hill equation. Curves were fitted using a non-linear least square fit with the Levenberg-Marquardt algorithm.

Percent Control (% Ctrl)

The compound(s) were screened at 10 µM and results for primary screen binding interactions are reported as '% Ctrl', where lower numbers indicate stronger hits in the matrix.

% Ctrl Calculation $$\left(\frac{\text{test compound signal} - \text{positive control signal}}{\text{negative control signal} - \text{positive control signal}}\right) \times 100$$

where:
test compound=compound submitted by Environmental Health Foundation
negative control=DMSO (100% Ctrl)
positive control=control compound (0%/Ctrl)

Figure 5:
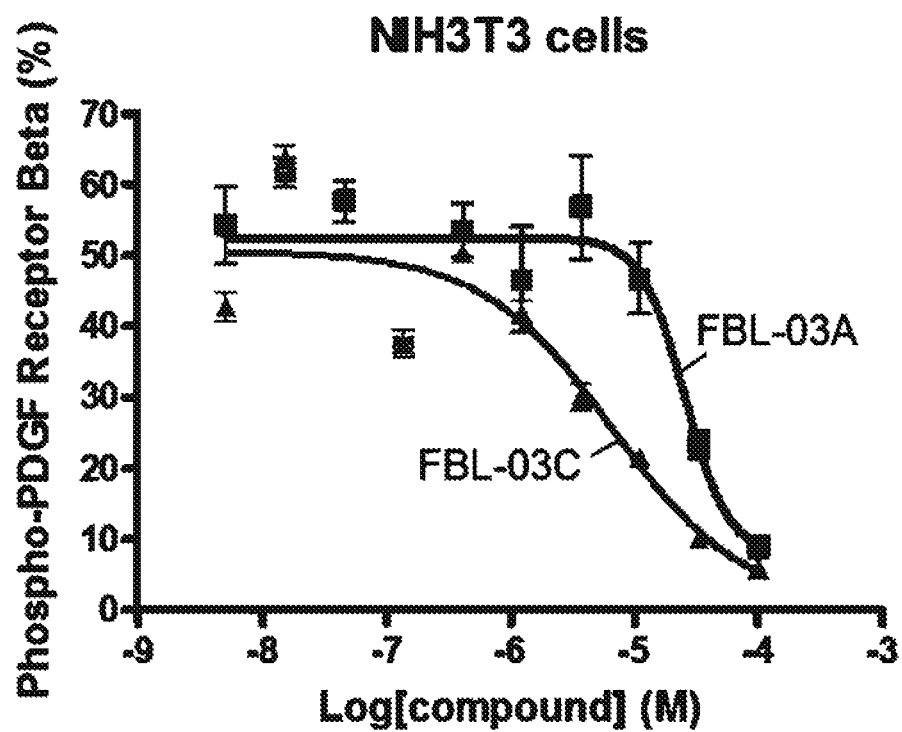
FIG. 5 is a graphical illustration of the results of the kinase inhibition by cannflavins presented in Table 1.

The results of the kinase inhibition by cannflavins are presented in Table 1 (above) and in FIG. 5. Inhibition of Sirtuins, matrix metalloproteinase, bromodomains was also confirmed using standard protocols and the results are present in Table 2.

PDGERb is implicated in a variety of myeloproliferatue disorders and cancers result from translocations that actuate.

PD Flab by fusion with proteins such as TELETV6, H2, CEV14/TRP11, rabaptin 5 and huntington interacting protein 1.

PD Flab is also overexpressed in metastatic medulloblastoma.

PDGERb is involved also in angiogenasis.

Bioactivity of the above-described compounds has been verified by an anticancer cell proliferation assay using the WST-1 (4-[3-(4-iodophenyl)-2-(4-nitrophenyl)-2H-5-tetrazolio]-1,3-benzene disulfonate) colorimetric assay by Roche Life Sciences. Anticancer activity was tested against several standard cancer cell lines including brain, breast, Kaposi sarcoma, leukemia, lung, melanoma, ovarian, pancreatic, colon and prostate cancer. Cells were trypsinized and plated into 96 well plates in 50 µl of media and incubated overnight. The next day approximately 18 hours after plating, 50 µl of media containing the required flavonoid-based pharmaceutical composition was added per well. Cells were plated at a density so that 72 hours post drug addition, the cells will be in log phase (500-2000 cells/well). The compounds and extracts were solubilized in Dimethyl sulfoxide (DMSO). The cells are allowed to proliferate for 72 hours 37° C. in humidified atmosphere of 5% $CO_2$. The experiment is terminated using WST-1 (Roche®) 10 µl per well and absorbance is read at 450 nm/690 nm. The effect of drugs on growth is assessed as percent of cell viability. The $IC_{50}$ values were determined from the extract dose versus control growth curves using Graphpad Prism® software. All experiments were carried out in duplicate and the mean results determined.

Figure 6:
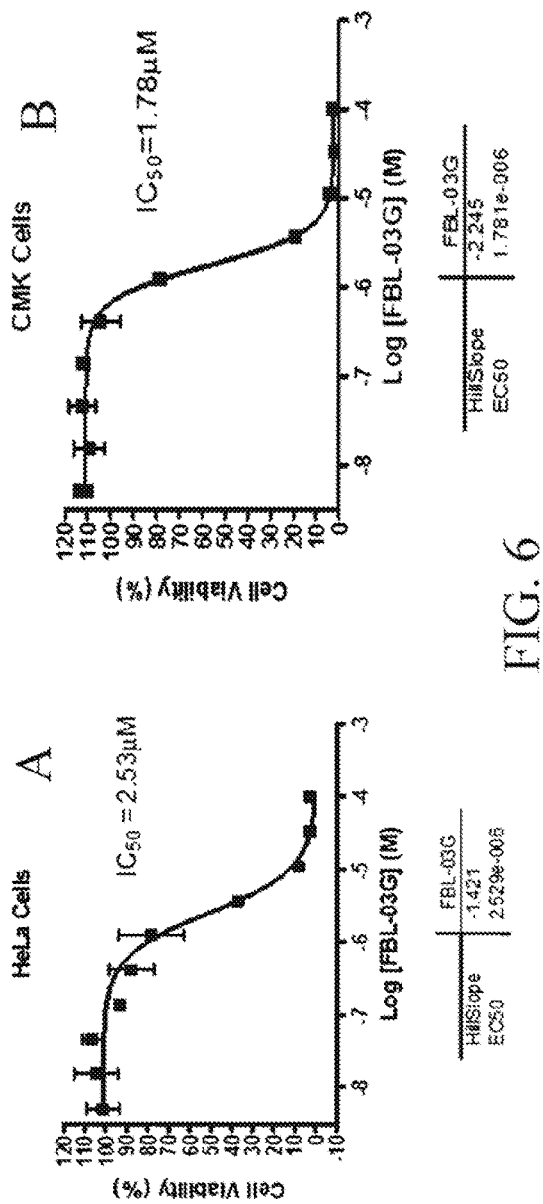
FIG. 6 is a graphical illustration of the results of the anticancer activity presented in Table 3 (Hela cells at A and CMK cells at B).
Figure 7:
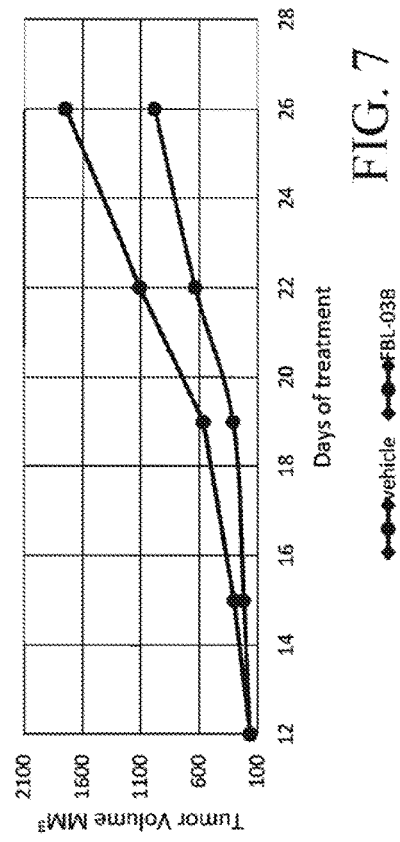
FIG. 7 is a graphical illustration of the results of the anticancer activity in mice.

The results of the anticancer activity are presented in Table 3 (above) and in FIG. 6, Hela cells shown at (A) and CMK cells at (B). To demonstrate a proof of concept in vivo, human pancreatic cancer xenograft CFPAC-1 cells implanted on scid mice were treated with FBL-03B and demonstrated significant inhibition of tumor compared to the control during 14 days of treatment. The results of the anticancer activity in mice are presented in FIG. 7.

It should now be apparent that the above-described invention provides a pharmaceutical composition for the prevention and treatment of disease with specific cannabis-based flavonoid compounds selected from among the groups of Apigenin, Cannflavin A, Cannflavin B, Cannflavin C, Chrysoeriol, Cosmosiin, Flavocannabiside, Kaempferol, Luteolin, Myricetin, Orientin, Isoorientin (Homoorientin), Quercetin, (+)-Taxifolin, Vitexin, and Isovitexin, a method for the prevention and treatment of disease using the specific cannabis-based flavonoid pharmaceutical compositions, a method for isolating the cannabis-based flavonoid pharmaceutical compositions from raw plant material, and a method for synthesizing said specific cannabis-based flavonoid pharmaceutical compositions.

Other embodiments of the invention will be apparent to those skilled in the art from consideration of the specification and practice of the invention disclosed herein. It is intended that the specification and examples be considered as exemplary only, with a true scope and spirit of the invention being indicated by the claims. In addition, as one of ordinary skill in the art would appreciate, any dimensions shown in the drawings or described in the specification are merely exemplary, and can vary depending on the desired application of the invention. Many variations and modifications of the embodiments described herein will be obvious to one of ordinary skill in the art in light of the above disclosure. The scope of the invention is to be defined only by the claims, and by their equivalents.

STATEMENT OF INDUSTRIAL APPLICABILITY

Certain cancers overexpress certain oncogenic factors including kinases, sirtuins, bromodomains, matrix metalloproteinases and BCL-2, and so these particular oncogenic factors are useful therapeutic targets. Cannabis flavonoids have been shown to have several pharmacological properties against these oncogenic factors, but different cancers respond differently to oncogenic agents and that the response to a combination of several such agents is unpredicatable. There would be great industrial applicability in the use a group of cannabis-based flavonoid pharmaceutical compositions selected from among the group of Apigenin, Cannflavin A. Cannflavin B, Cannflavin C, Chrysoeriol, Cosmosiin, Flavocannabiside. Kaempferol, Luteolin, Myricetin, Orientin, Isoorientin (Homoorientin), Quercetin, (+)-Taxifolin, Vitexin. and Isovitexin, for the prevention and treatment of certain cancers treatable by targeting kinases, sirtuins, bromodomains, matrix metalloproteinases and BCL-2. Some of the cancers that can be treated by use of cannabis flavonoids based on the inhibition of these therapeutic targets include brain, breast, colon, renal, liver, lung, pancreatic, prostate, leukemia, melanoma as well as any other cancers that overexpress the oncogenic factors inhibited by cannabis flavonoids.

We claim:

1. A method of treating pancreatic cancer, the method comprising administering to a patient in need thereof a cannabis-based flavonoid pharmaceutical composition having a flavone backbone according to chemical structure as shown below, or any pharmaceutically acceptable salt thereof:

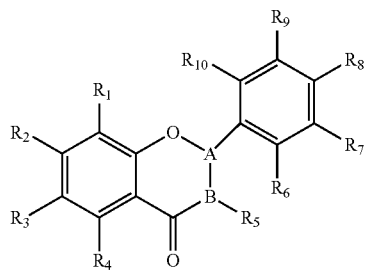

wherein R1-R10 may be any one or more substituents selected from the group consisting of a hydrogen molecule (H), a hydroxide molecule (OH), a methyl group comprising one carbon atom bonded to three hydrogen atoms (CH3), a methoxy group, a carboxyl group (COOH), chlorine (Cl), Bromine (Br), Fluorine (F), Glutamic acid (Glu) wherein one of R1 or R3 must be either 3-methyl-2-butenyl or 3,7-dimethyl-2,6-octenyl, and any salts of the foregoing, and the carbon-to-carbon A and B bond may each be either a single flavanone bond or a double flavone bond.

2. A method of treating pancreatic cancer, comprising administering to a patient in need thereof a composition having a specific chemical structure as shown below:

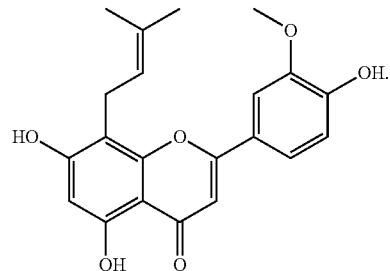 [SMILES: COc1cc(-c2cc(=O)c3c(O)cc(O)c(CC=C(C)C)c3o2)ccc1O]

* * * * *